(12) United States Patent
Meindersma

(10) Patent No.: US 7,475,689 B2
(45) Date of Patent: Jan. 13, 2009

(54) DENTAL FLOSS HOLDER

(76) Inventor: Jonathan Meindersma, 20 Maple St., West Boylston, MA (US) 01583

( * ) Notice: Subject to any disclaimer, the term of this patent is extended or adjusted under 35 U.S.C. 154(b) by 0 days.

(21) Appl. No.: 10/860,101

(22) Filed: Jun. 3, 2004

(65) Prior Publication Data

US 2005/0039772 A1    Feb. 24, 2005

Related U.S. Application Data

(60) Provisional application No. 60/475,236, filed on Jun. 3, 2003.

(51) Int. Cl.
*A45D 7/00* (2006.01)
*A61C 15/00* (2006.01)

(52) U.S. Cl. ........................................ 132/200; 132/321
(58) Field of Classification Search ......... 132/321–329, 132/200; D28/65–68
See application file for complete search history.

(56) References Cited

U.S. PATENT DOCUMENTS

| | | | | |
|---|---|---|---|---|
| D41,124 S | * | 1/1911 | Morgan | D8/38 |
| 2,180,522 A | * | 11/1939 | Henne | 132/323 |
| 3,747,778 A | * | 7/1973 | Collins, Jr. | 414/678 |
| D397,744 S | * | 9/1998 | Brummer | D21/615 |
| D408,589 S | * | 4/1999 | Chodorow | D28/67 |
| 6,003,525 A | * | 12/1999 | Katz | 132/321 |
| 6,085,760 A | * | 7/2000 | Chodorow | 132/323 |
| D443,113 S | * | 5/2001 | Chodorow | D28/67 |
| D455,232 S | * | 4/2002 | Chodorow | D28/67 |
| D456,566 S | * | 4/2002 | Chodorow | D28/67 |

* cited by examiner

*Primary Examiner*—Robyn Doan
(74) *Attorney, Agent, or Firm*—Pandiscio & Pandiscio

(57) ABSTRACT

A dental floss holder is disclosed shaped like a dinosaur bone, and configured to be assembled with other dental floss holders shaped like a dinosaur bone, so as to form a dinosaur skeleton. The dinosaur skeleton comprises a plurality of dental floss holders, wherein each dental floss holder is shaped like a dinosaur bone.

7 Claims, 19 Drawing Sheets

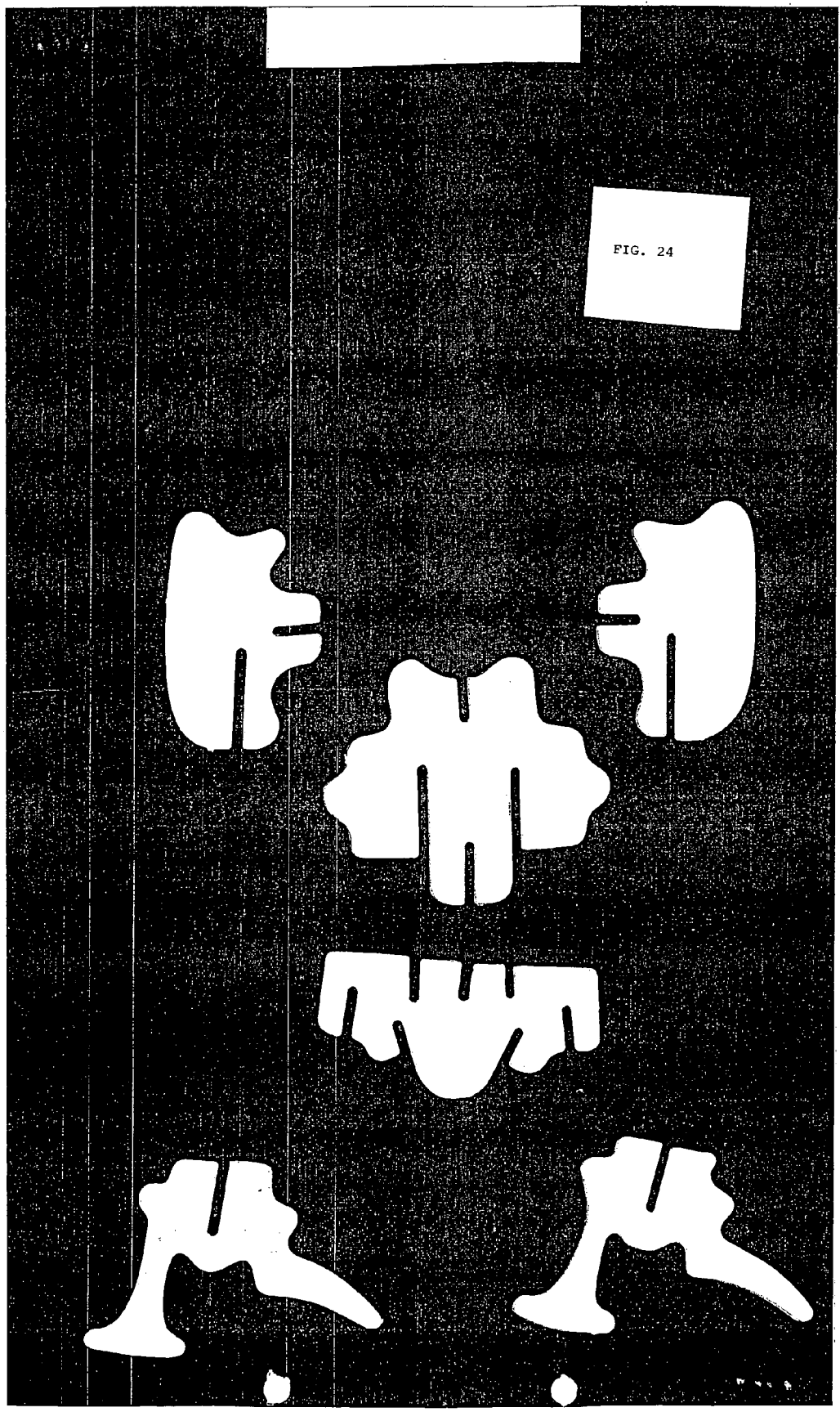

DENTAL FLOSS HOLDER

REFERENCE TO PENDING PRIOR PATENT APPLICATION

This patent application claims benefit to prior U.S. Provisional Patent Application Ser. No. 60/475,236, filed Jun. 3, 2003 by Jonathan Meindersma for FLOSSILS™, which patent application is hereby incorporated herein by reference.

FIELD OF THE INVENTION

This invention relates to dental products in general, and more particularly to dental floss holders of the sort used to support dental floss during use.

BACKGROUND OF THE INVENTION

When young children go to the dentist, they are encouraged to floss as well as to brush their teeth. In many cases the children may use dental floss holders to assist them in their flossing. Dental floss holders are small plastic handles which present a piece of dental floss for insertion between the teeth.

Many children also have a keen interest in dinosaurs, taking great joy in learning about them, assembling puzzles of dinosaurs and dinosaur skeletons, and in playing computer games in which they "dig up" and "assemble" fossils.

SUMMARY OF THE INVENTION

The present invention utilizes children's fascination with dinosaurs to encourage them to floss. More particularly, FLOSSILS™ are a new product which are dental floss holders shaped like dinosaur bones, and capable of being collected and assembled so as to form a variety of complete dinosaur skeletons. Children will look forward to flossing with FLOSSILS™ because after each flossing session, the used floss is removed, leaving the dinosaur bone-shaped floss holder, which the children then collect and assemble so as to form complete dinosaur skeletons.

BRIEF DESCRIPTION OF THE DRAWINGS

FIGS. 22-24 are images of individual FLOSSILS™.

DETAILED DESCRIPTION OF THE INVENTION

A FLOSSIL™ is a dental floss holder of a particular size, shape and sufficient rigidity to enable the user to apply sufficient pressure at the tooth-floss interface to scrape tooth surfaces with the floss. The dental floss is bonded into the holder in the manufacturing process, leaving no loose ends but embedding them under tension in the holder. The floss is thus held taut, but not overly tight, so as to permit flexion to facilitate the cleaning of curved tooth surfaces above and below the gumline.

FLOSSILS™ have an opening across which the dental floss is strung, to permit the user to work the floss between teeth. The opening allows adequate clearance to reach between molars.

The shape of a FLOSSIL™ is distinctive, being similar in appearance (but not size) to various bones of a number of different dinosaurs and other prehistoric creatures and things susceptible to having become fossilized. More particularly, FLOSSIL™ shapes vary according to the shapes of different dinosaur species and genus and their differing bones or other fossilized materials. FLOSSILS™ therefore may be shaped as skulls, jawbones, leg or arm bones, hand/claw/foot bones, or bones of the neck, spine, tail, torso, fin,. or wing, depending on the anatomy of the creature or thing depicted.

Figure 1:
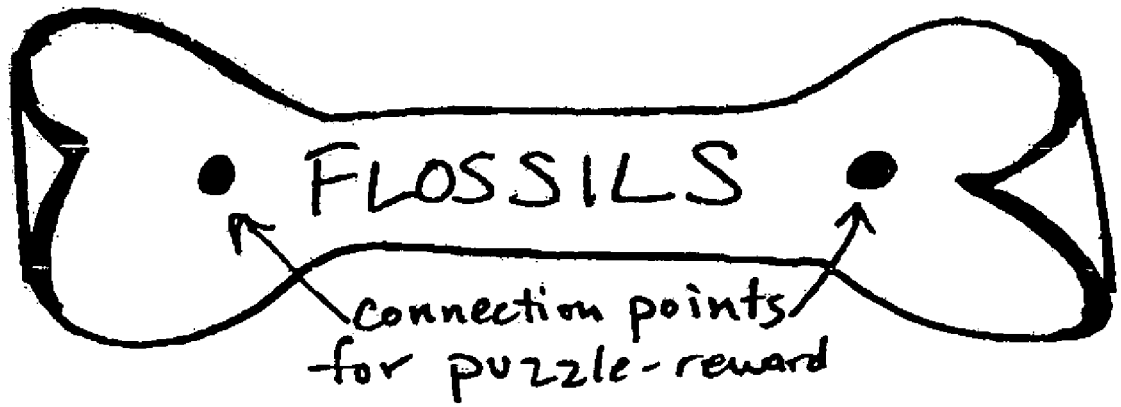
FIG. 1 shows an individual FLOSSIL™ detail.
Figure 2:
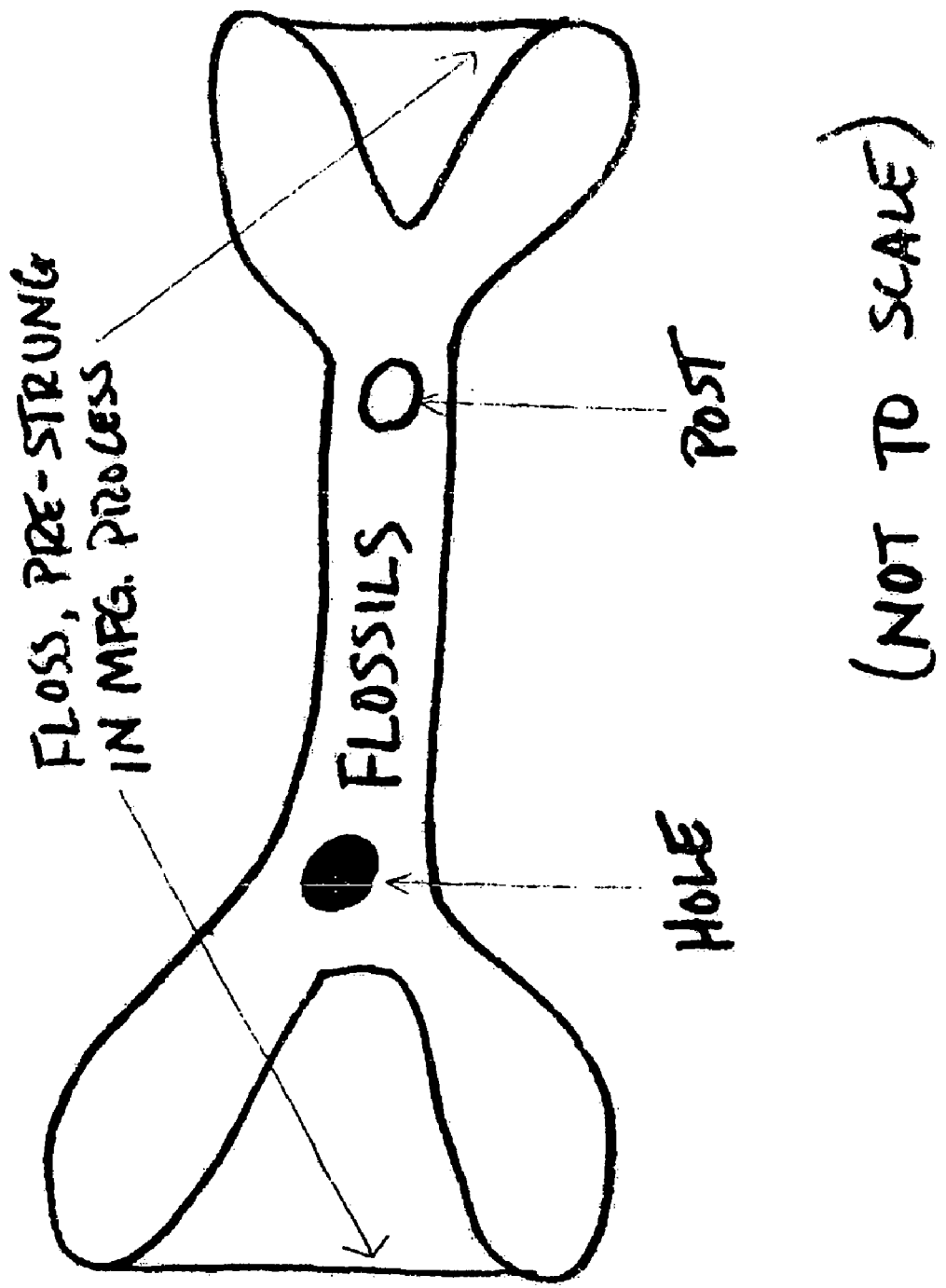
FIG. 2 shows an individual FLOSSIL™ detail.
Figure 3:
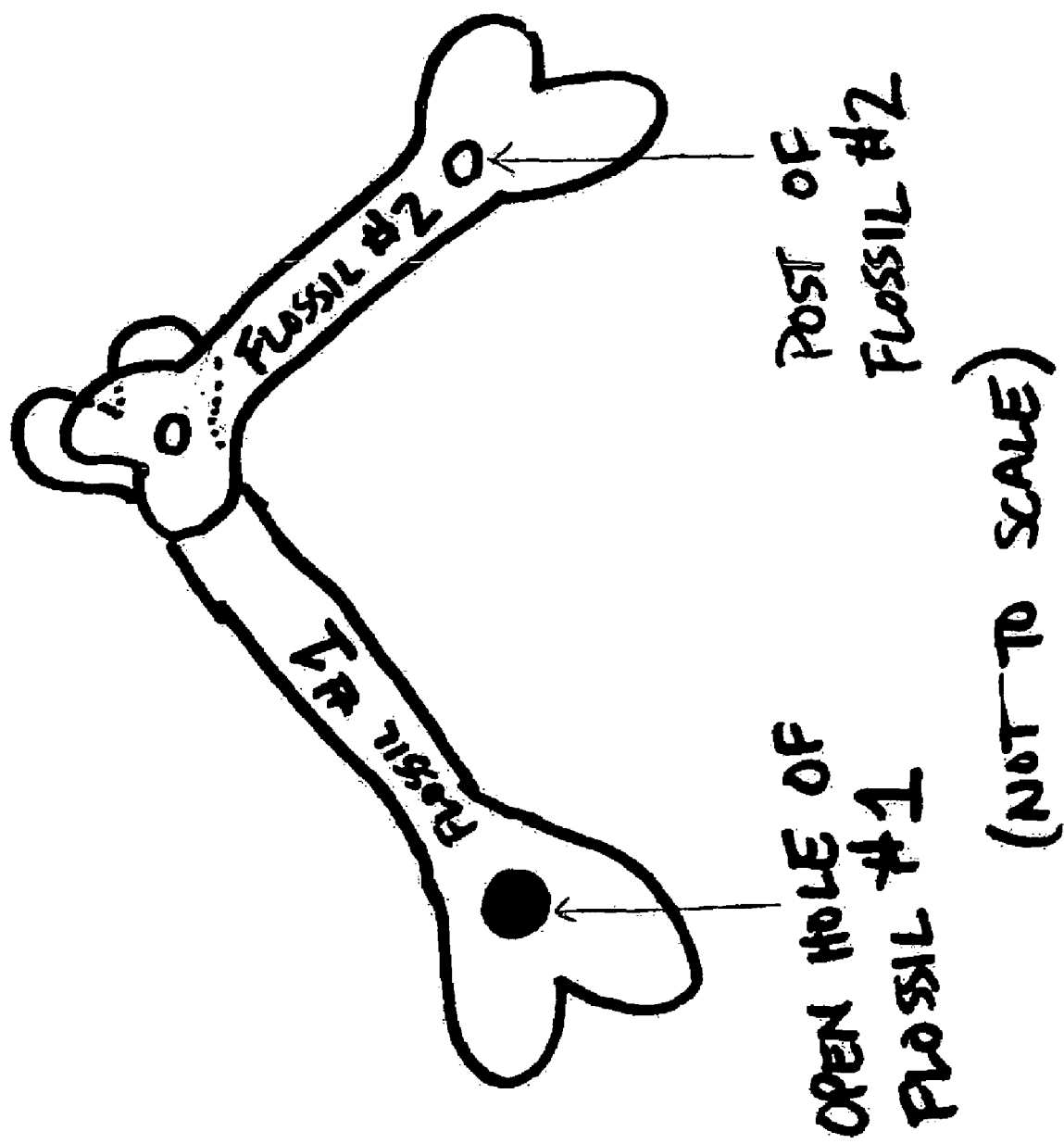
FIG. 3 shows an example of two FLOSSILS™ joined together.
Figure 4:
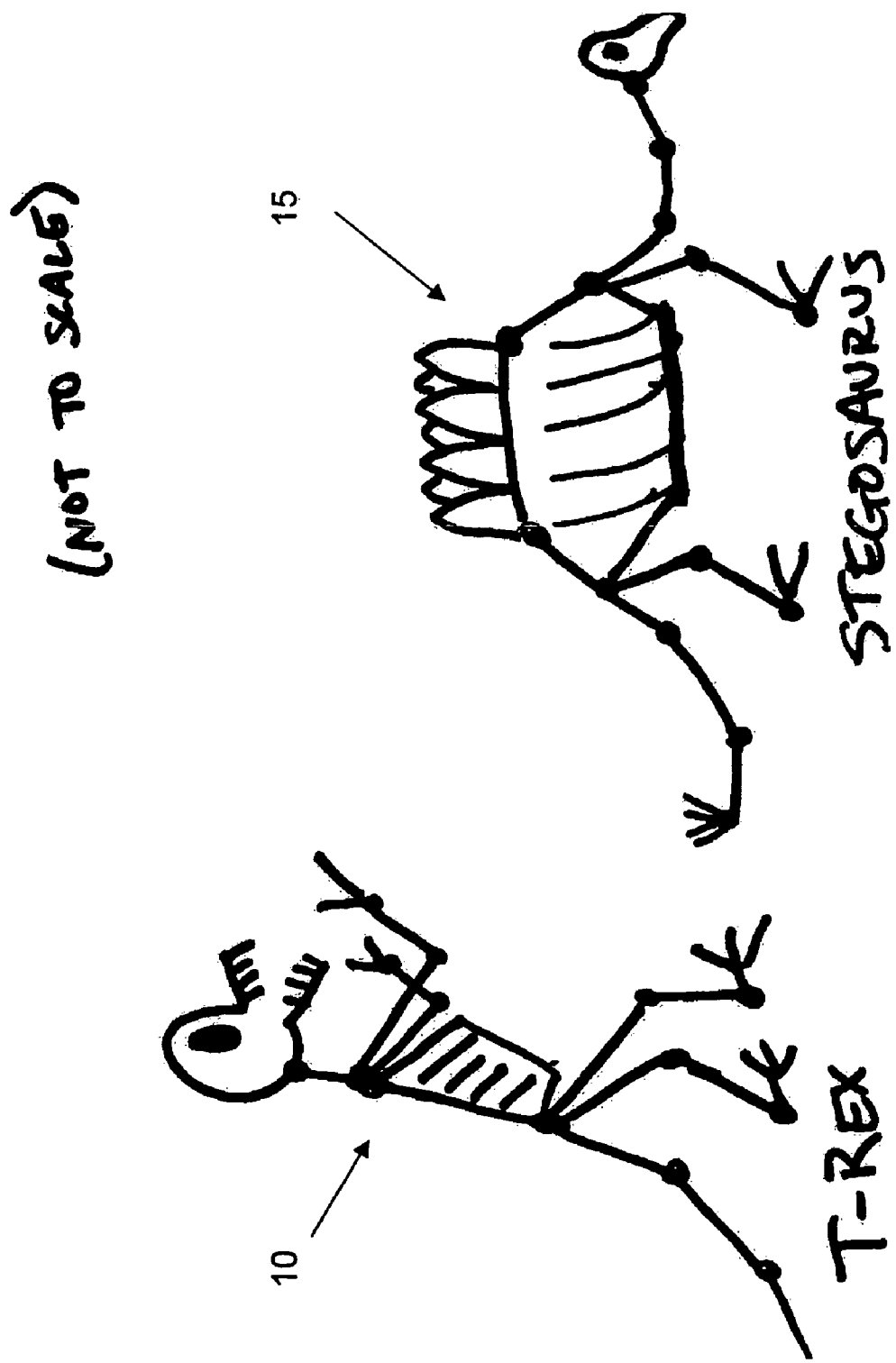
FIG. 4 shows sample schematic drawings of fully assembled skeletons showing FLOSSIL™ connection points.

FLOSSILS™ also have posts and holes formed in the injection molding process, placed so as to enable the user to join a number of separate FLOSSILS™ together by inserting the post on FLOSSIL™ #1 into the hole in FLOSSILS™ #2, and so on. The hole of FLOSSIL #2 may also be placed over post of FLOSSIL #1, effecting a pivoting joint. When assembled according to instructions provided on the package, the FLOSSILS™ will be in the form and shape, generally, of a skeleton of a dinosaur or other prehistoric creature. A sampling of such creatures might include, by way of example but not limitation, a Tyrannosaurus Rex 10, a Pteranodon, a Stegosaurus 15, a Triceratops, an Apatosaurus, a Diplodocus, an Ankylosaurus, an Iguanodon, a Velociraptor, a Brachiosaurus, a Plesiosaurus, a Mammuthus, or a Smilodon (Sabretooth). (See FIG. 4.)

FLOSSILS™ can be disposable or saved for puzzle-like assembly, making entire skeletons as a reward to kids for flossing.

A FLOSSIL™ may have floss strung on one or both ends, depending on its shape and the place it is to occupy in the puzzle. FLOSSILS™ need not be any particular color, although white and off-white are typically the most desirable. The pieces may also be luminescent if desired, so as to create a glow-in-the-dark puzzle as well.

Figure 10:
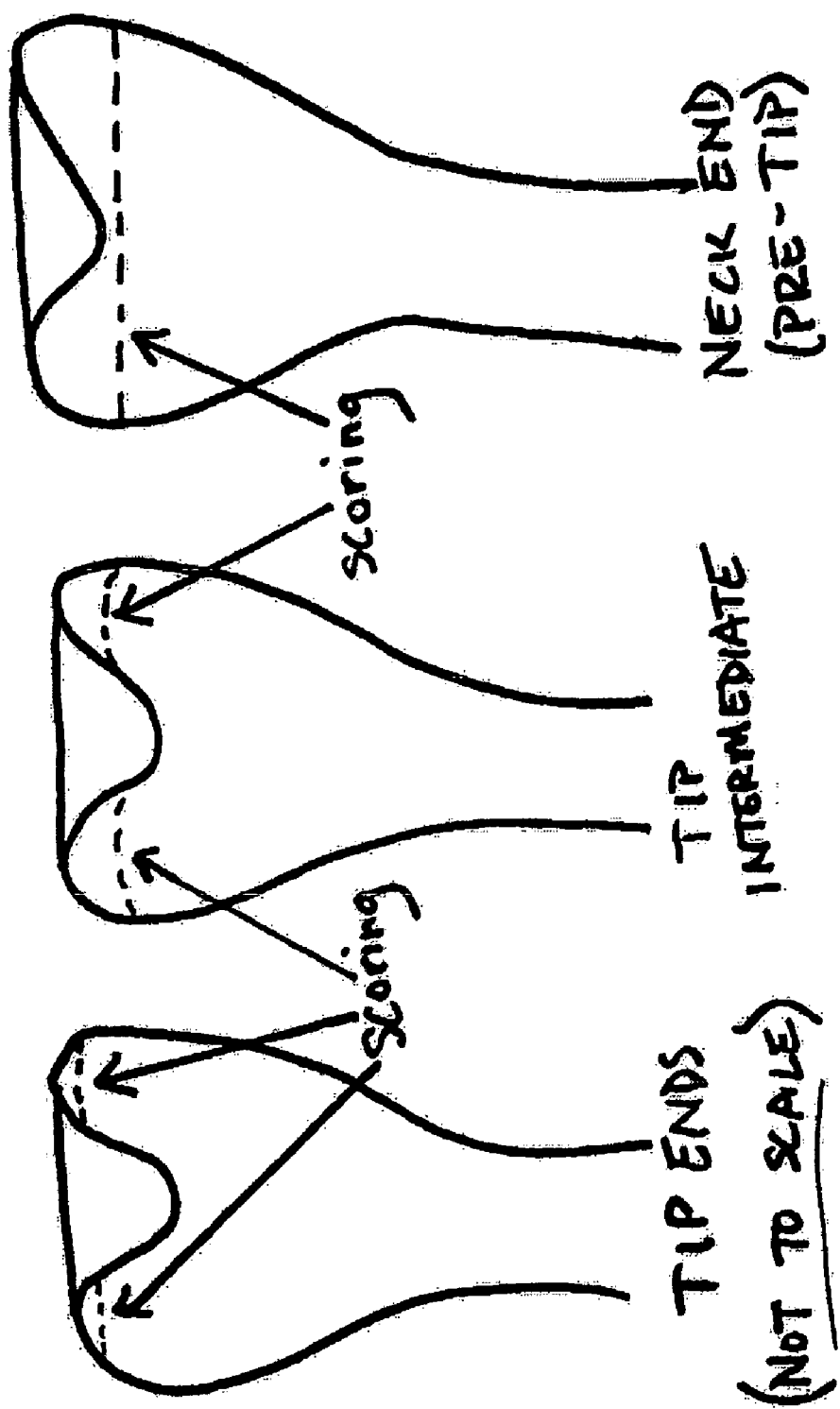
FIG. 10 shows possible locations for scoring the FLOSSIL™ to permit easy removal of the floss-embedded ends from the remainder of the unit.
Figure 11:
FIGS. 11-21 are photographs of fully assembled skeletons.
Figure 12:
Figure 13:
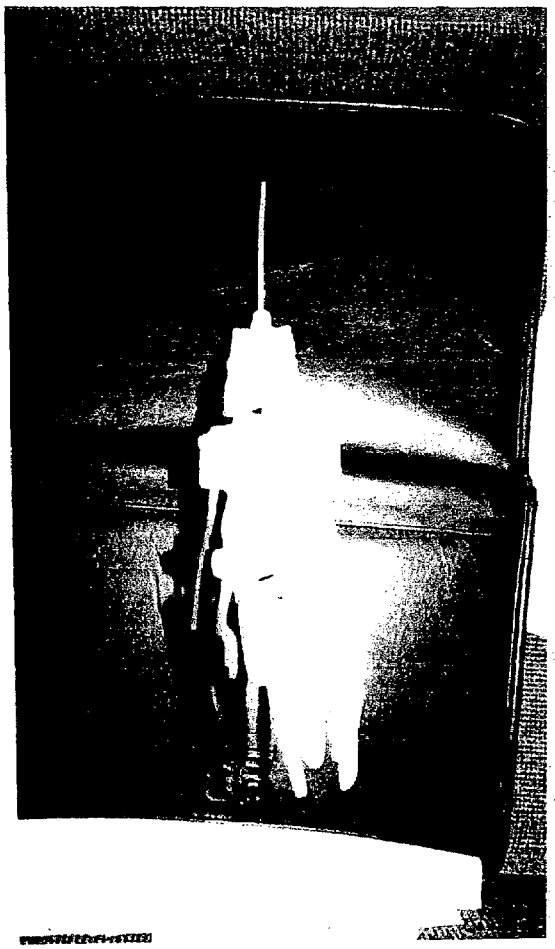
Figure 14:
Figure 15:
Figure 16:
Figure 17:
Figure 18:
Figure 19:
Figure 20:
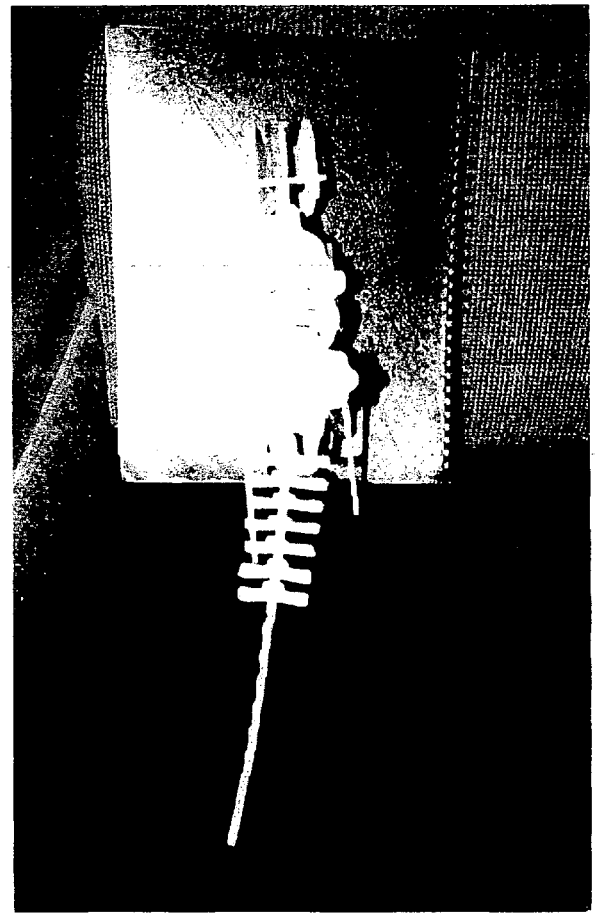
Figure 21:
Figure 22:
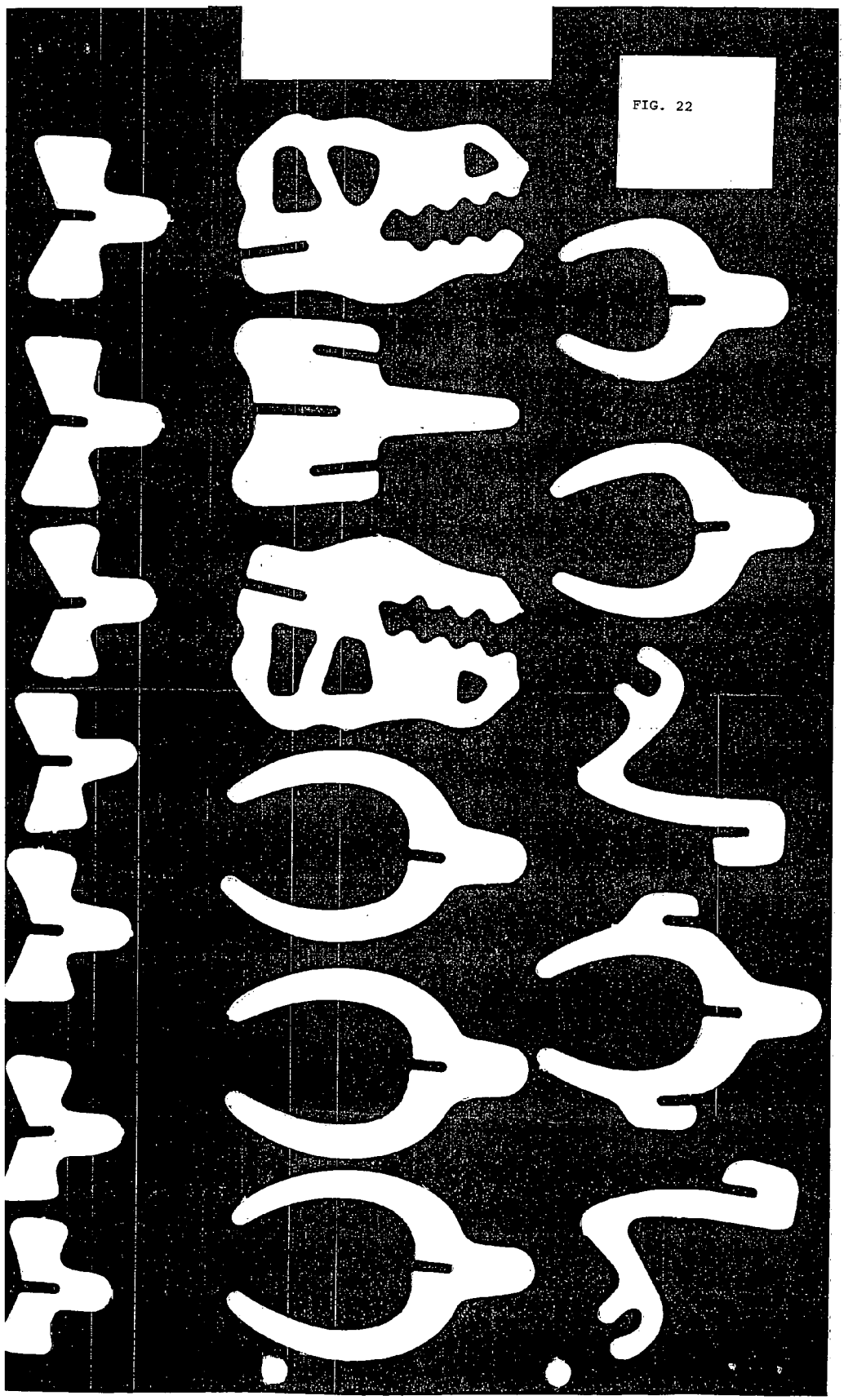
Figure 23:
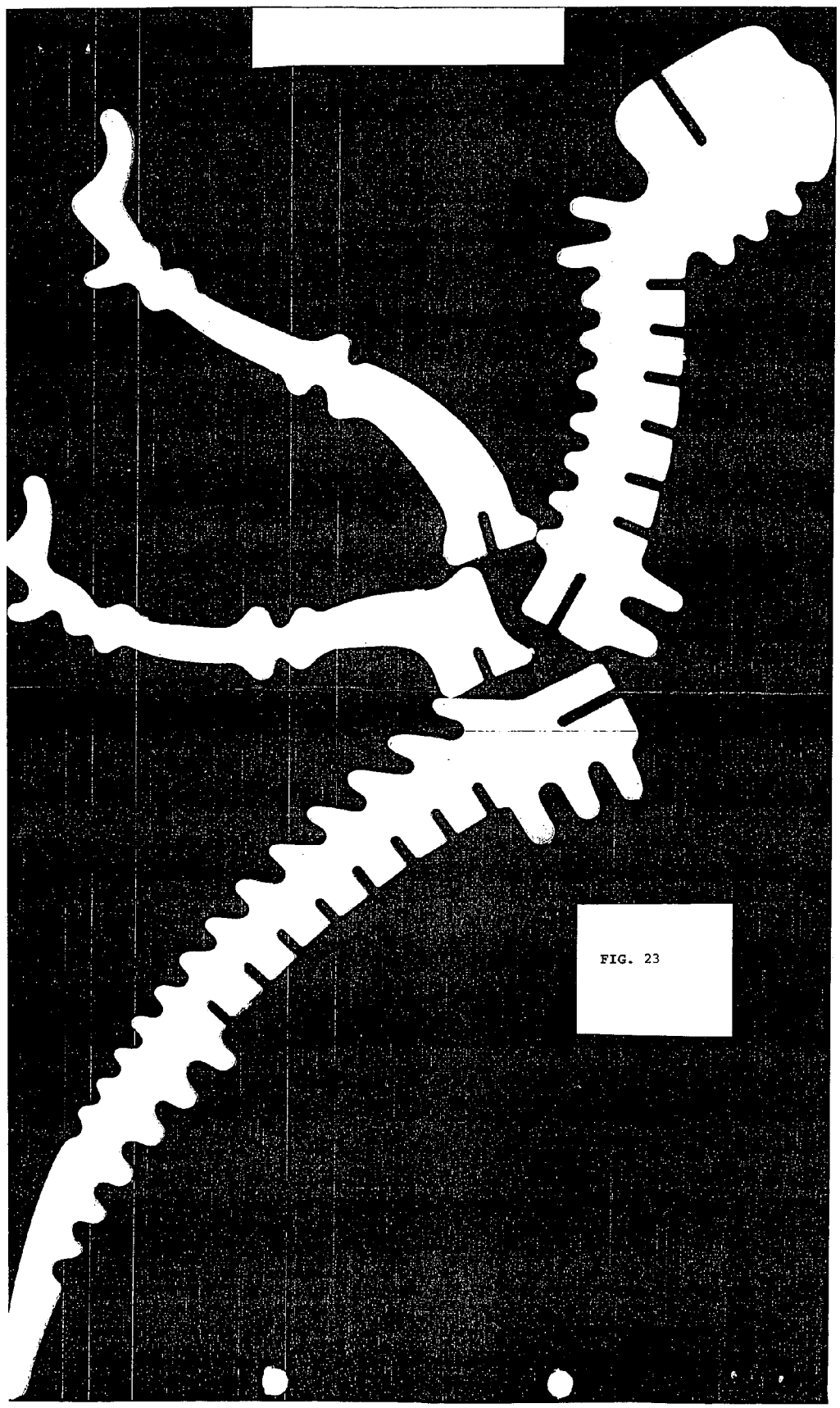

After use, the floss is removed from the FLOSSIL™, either by cutting it off flush with the FLOSSIL™ surface or by scoring the FLOSSIL™ during the manufacturing process to enable the floss-embedded ends to be broken off. FIG. 10 illustrates three of a number of points which are possible and which would permit the floss embedded ends of the FLOSSIL™ to be broken off, leaving the user with a floss-less FLOSSIL™ puzzle piece. Either method leaves the user with a FLOSSIL™ puzzle piece which no longer contains any exposed dental floss.

Figure 5:
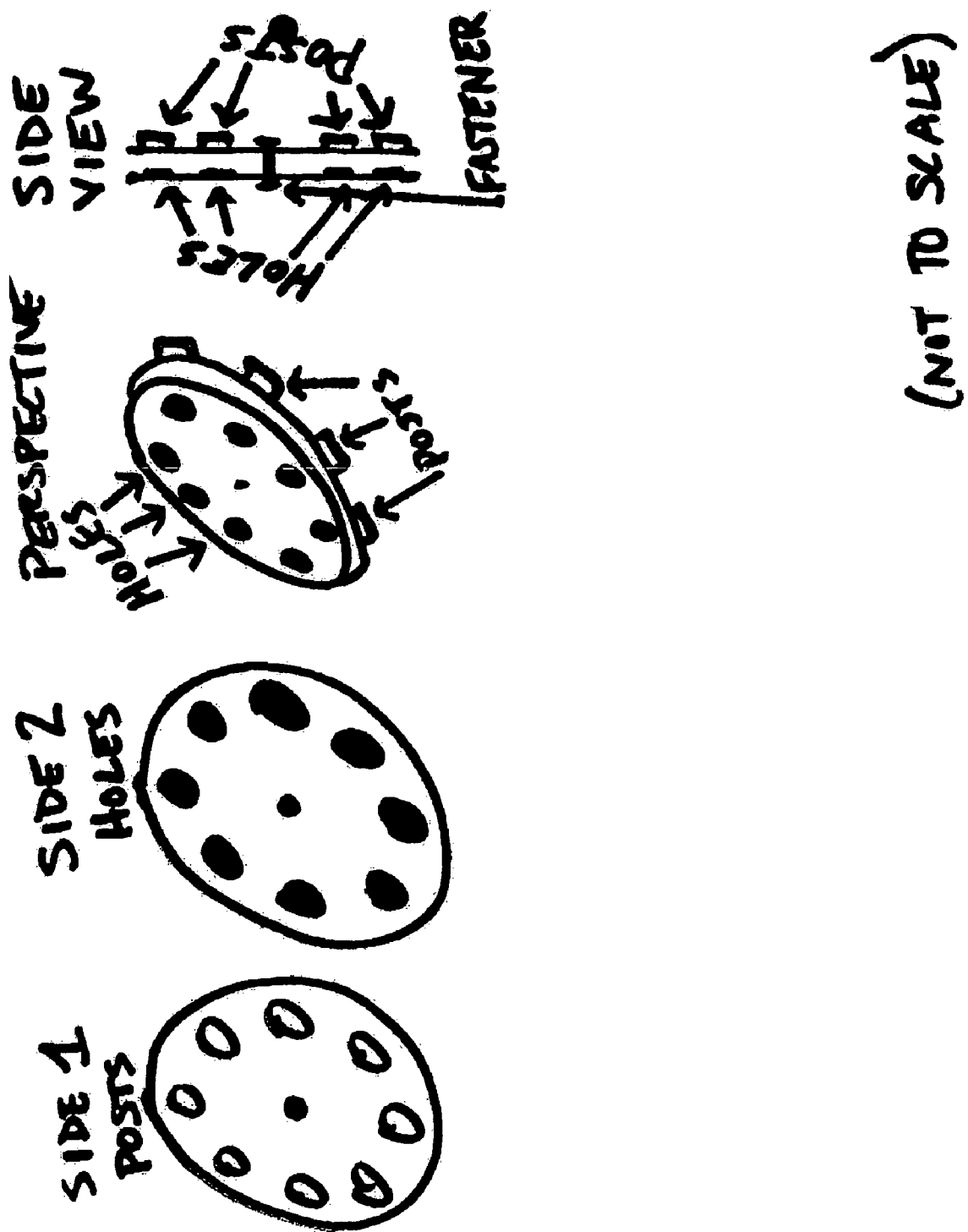
FIG. 5 shows FLOSSIL™ Fasteners Discs.
Figure 6:
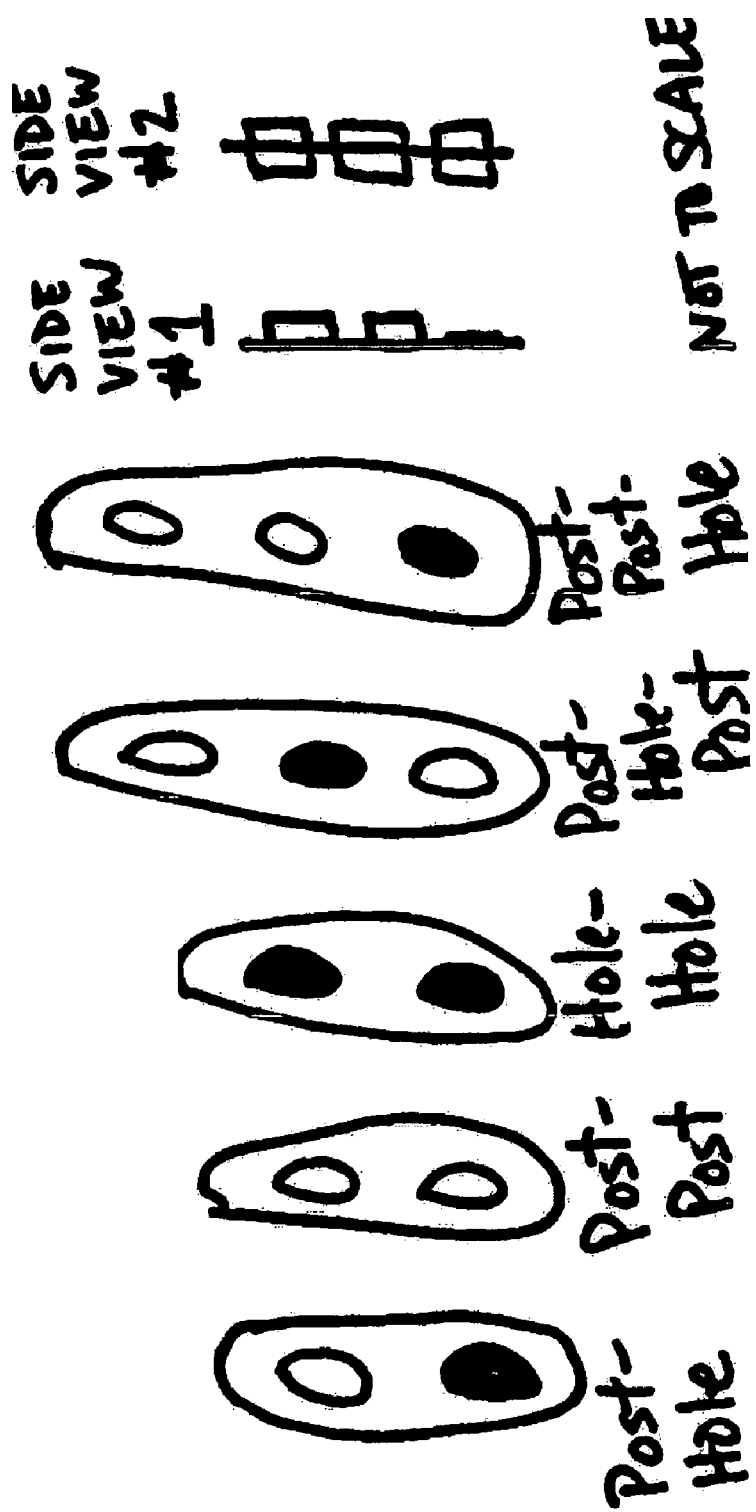
FIG. 6 shows a FLOSSIL™ Fastener—Rigid (1)
Figure 7:
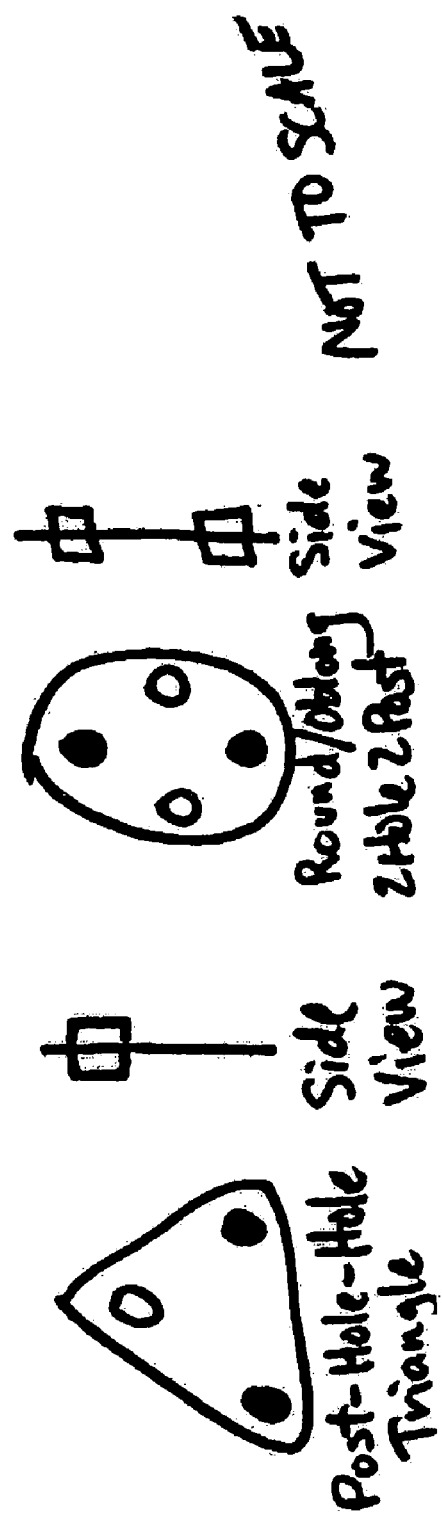
FIG. 7 shows a FLOSSIL™ Fastener—Rigid (2)

It is also possible to connect together separate FLOSSIL™ elements with arrangements other than the post-and-hole arrangement discussed above. By way of example but not limitation, "FLOSSIL™ Fasteners" can be provided in a rigid form as well as in a dual parallel disc form which permits rotation and flexibility. See FIGS. 5-7.

Disc FLOSSIL™ Fasteners are discs made of the same or similar material as a FLOSSIL™, though they may be clear, colored, or white/luminescent. They are mounted in parallel by a metal or plastic fastener through both centers. One disc has holes and the other disc has posts. This permits joining multiple FLOSSILS™ at a common connection point, allowing a multitude of angles of juncture and free adjustment thereof. Discs also may be locked in place (preventing rotation) by inserting a post on the reverse of side 1 through a hole in side 2.

Rigid FLOSSIL™ Fasteners are made of the same or similar material as FLOSSIL™, though they may be clear, colored, or white/luminescent. Rigid FLOSSIL™ Fasteners may come in a variety of shapes and sizes, and have one or more holes and/or posts, in various arrangements and configurations, such as H-P (Hole-Post), P-P, H-H, P-P-H, H-H-P, P-P-P, H-H-H, etc.. See FIG. 6.

Rigid FLOSSIL™ Fasteners may also be round, triangular, or appear in any number of shapes and sizes to permit planned and unplanned (i.e., creative, fanciful, or imaginative) connection of FLOSSILS™. See FIG. 7.

Figure 8:
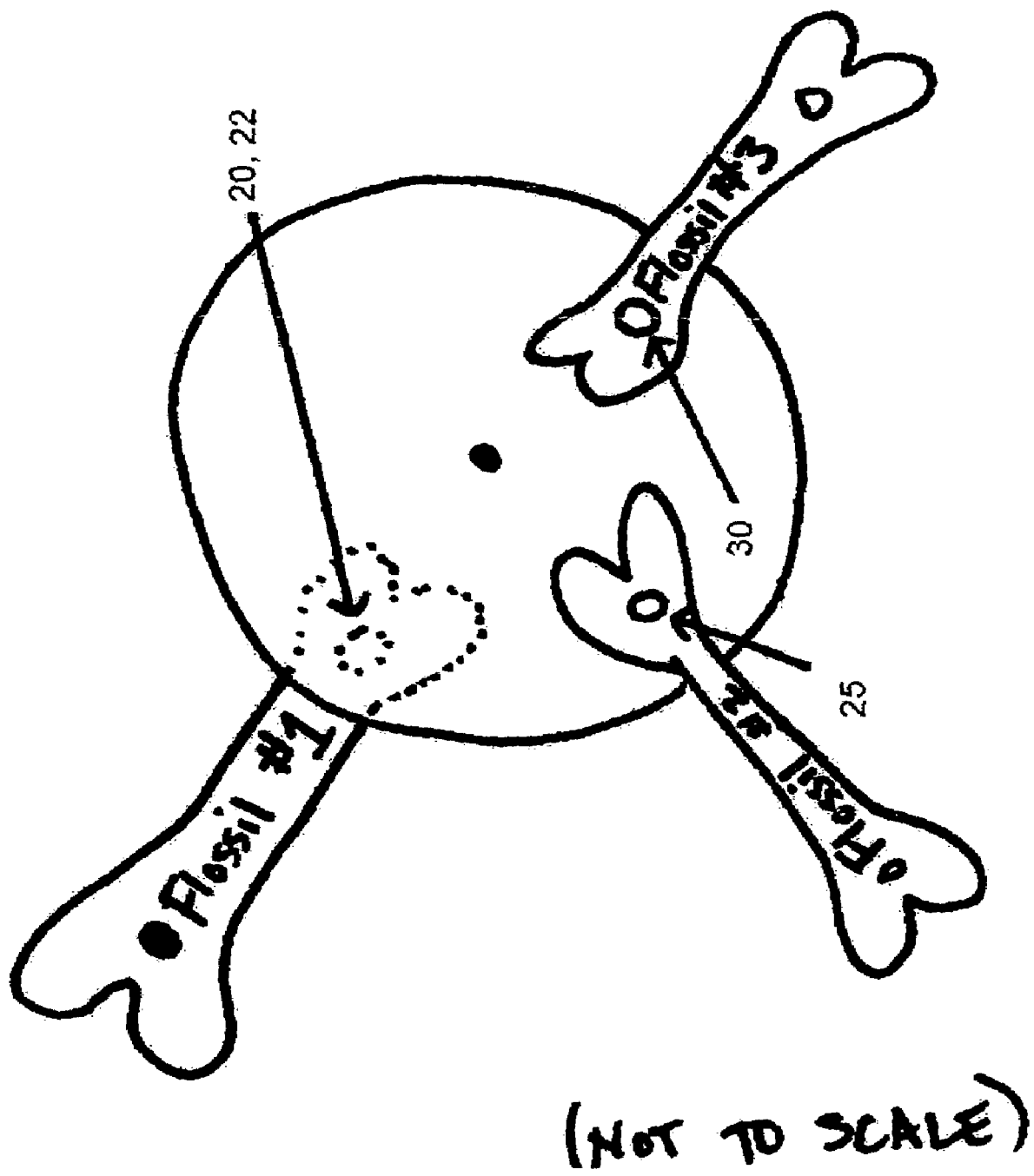
FIG. 8 shows an example of 3 FLOSSILS™ joined using a FLOSSIL™ Fastener disc.

FIG. 8 shows an example of three FLOSSILS™ joined using FLOSSIL Fastener Disc. Post 20 of FLOSSIL #1 is inserted through hole 22 on the hole side of FLOSSIL Fastener Disc. Holes 25, 30 of FLOSSILS #2 and #3 are placed over posts of FLOSSIL Fastener disc.

Figure 9:
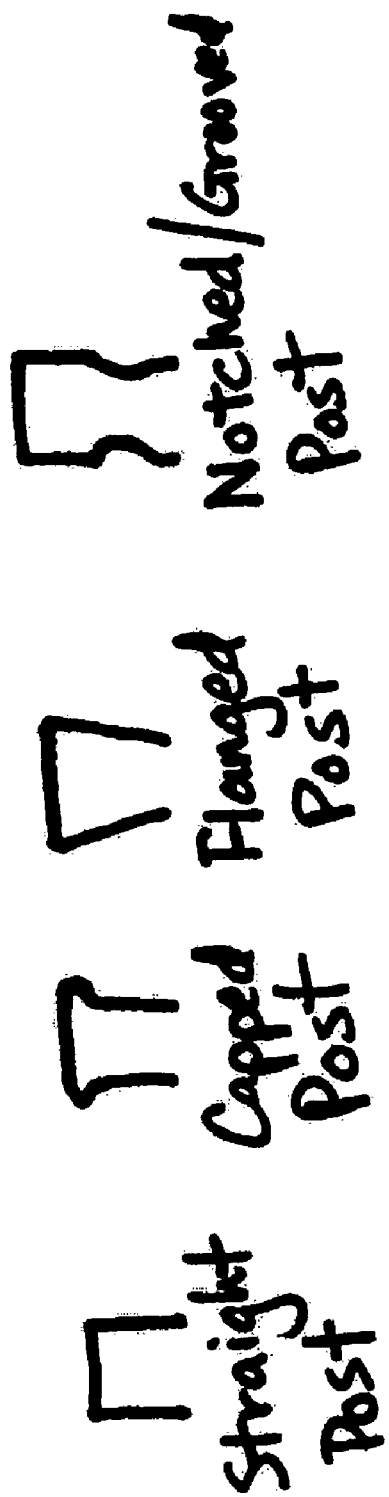
FIG. 9 shows FLOSSIL™ Post detail.

FIG. 9 shows FLOSSIL Post Detail. Posts on FLOSSILS™ and FLOSSIL Fasteners may be of any of the post designs shown in FIG. 9.

What is claimed is:

1. A method for forming a complete dinosaur skeleton from a plurality of dental flossers, the method comprising:
   providing a plurality of dental flossers, wherein each of the dental flossers comprises:
      a dental floss holder shaped like a dinosaur bone;
      a portion of dental floss removably attached to the dental floss holder; and
      a connector mounted to the dental floss holder for connecting that dental floss holder to other dental floss holders;
   removing the portion of dental floss from the dental floss holder; and
   connecting one dental floss holder to another dental floss holder; and
   continuing the foregoing process until a complete dinosaur skeleton is assembled.

2. A method according to claim 1 wherein the shape of the dental floss holders is selected from the group consisting of: skulls, jawbones, leg bones, arm bones, hand bones, claw bones, foot bones and bones of the neck, spine, tail, torso, fin and wing.

3. A method according to claim 1 wherein the connector comprises at least one selected from the group consisting of a male member and a female member.

4. A method according to claim 1 wherein the connector comprises at least one selected from the group consisting of a post and a hole.

5. A method according to claim 4 wherein the dental floss holders are joined together by inserting the post of one connector of one dental floss holder into the hole in another connector of another dental floss holder.

6. A method according to claim 1 wherein the plurality of dental flossers are provided in a package comprising the elements necessary to form a complete dinosaur skeleton.

7. A method according to claim 6 wherein the package comprises instructions for assembling the plurality of dental floss holders into a complete dinosaur skeleton.

* * * * *